United States Patent [19]
Crittendon et al.

[11] Patent Number: 6,064,797
[45] Date of Patent: May 16, 2000

[54] VOLUMETRIC FLOW EQUALIZING DRIVE CONTROL WHEEL

[75] Inventors: Joe C. Crittendon, Southlake; Harry C. Copp; Roberta Stavely, both of Carrollton; David J. Harrison, Irving, all of Tex.

[73] Assignee: B. Braun Medical, Inc., Bethlemen, Pa.

[21] Appl. No.: 09/169,900

[22] Filed: Oct. 12, 1998

[51] Int. Cl.⁷ ...................................................... H02P 5/00
[52] U.S. Cl. ............................................. 388/800; 417/22
[58] Field of Search .................................... 388/800, 907, 388/909; 318/767, 772; 417/1, 7, 18, 20, 22, 23, 44.1, 321; 604/9

[56] References Cited

U.S. PATENT DOCUMENTS

| | | | |
|---|---|---|---|
| 3,368,134 | 2/1968 | Mead, Jr. et al. | 318/318 |
| 4,277,226 | 7/1981 | Archibald | 417/38 |
| 4,443,216 | 4/1984 | Chappell | 604/67 |
| 4,496,351 | 1/1985 | Hillel et al. | 604/250 |
| 4,561,830 | 12/1985 | Bradley | 417/474 |
| 4,565,542 | 1/1986 | Berg | 604/131 |
| 4,596,550 | 6/1986 | Troutner | 604/5 |
| 4,601,702 | 7/1986 | Hudson | 604/246 |
| 5,261,877 | 11/1993 | Fine et al. | 604/49 |
| 5,279,556 | 1/1994 | Goi et al. | 604/67 |
| 5,370,612 | 12/1994 | Maeda et al. | 604/67 |
| 5,457,373 | 10/1995 | Heppe et al. | 318/772 |
| 5,554,013 | 9/1996 | Owens et al. | 417/413.1 |
| 5,645,531 | 7/1997 | Thompson et al. | 604/67 |

Primary Examiner—Robert E. Nappi
Assistant Examiner—Rina I. Duda
Attorney, Agent, or Firm—Gardere & Wynne, L.L.P.; John W. Montgomery

[57] ABSTRACT

A rotation control for a device to be rotated includes a variable speed DC motor having a constant rotational speed upon receiving a selected fixed voltage electrical input power from an adjustable electrical input power supply connected to the motor for supplying the selected fixed voltage. A switch circuit is connected between the motor and the power supply activatable in response to a first electrical signal to turn the motor "on" and activatable in response to a second electrical signal to turn the motor "off". A selectable frequency, regular interval electrical signal device is connected to the switch circuit to provide electrical signals to activate the switch circuit to turn the motor "on" at regular intervals. An encoder wheel is coupled to the device to be rotated and to the motor for rotation of the timing disk at a speed proportional to the constant rotational speed of the motor. The timing disk has a plurality of openings around the disk with predetermined spacing there between. The spacing corresponds to a desired amount of device rotation. A light sensor is operatively positioned adjacent to the encoder wheel for detecting the spaced openings and connected to the switch circuit to provide the electrical signal to turn the motor off each time a next one of the openings is detected by the sensor thereby allowing the device to traverse the desired amount of device rotation during each regular interval that the motor is turned on.

12 Claims, 5 Drawing Sheets

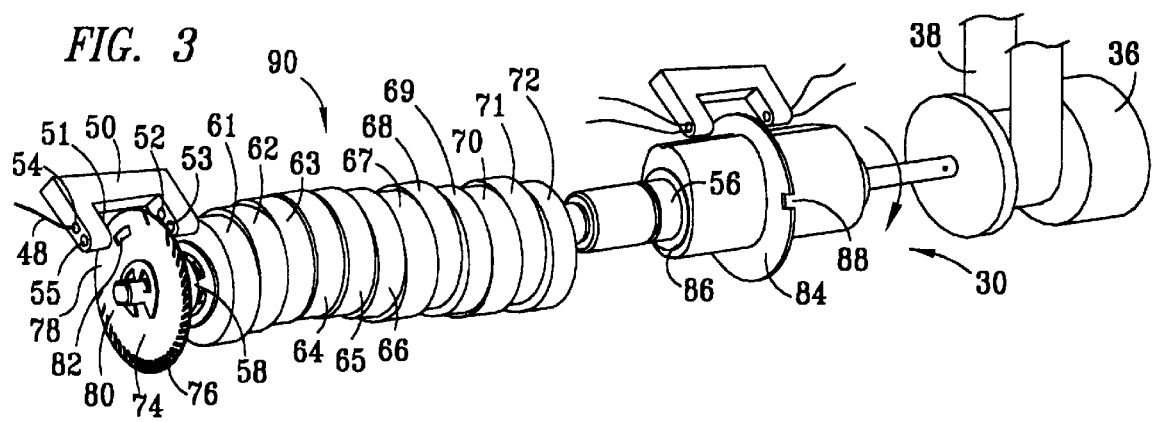
FIG. 3
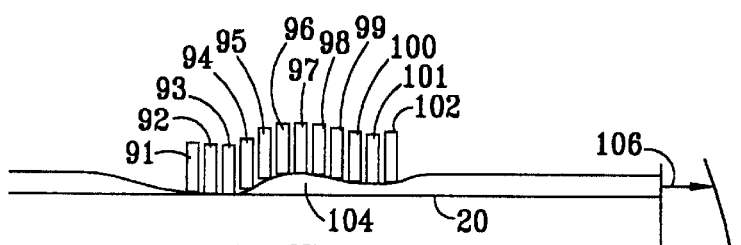
FIG. 4
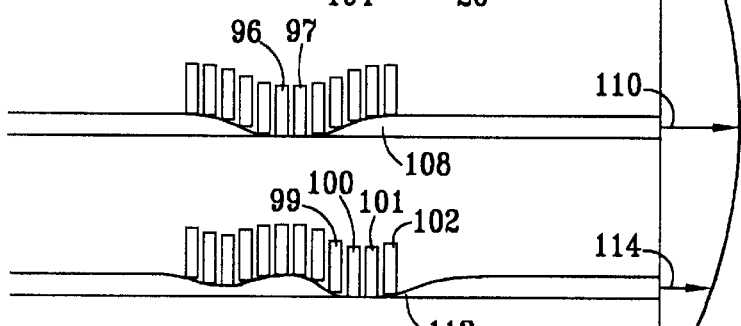
FIG. 5
FIG. 6
FIG. 7
FIG. 8
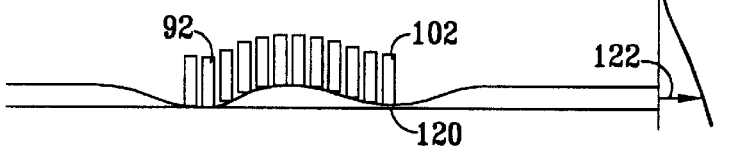

VOLUMETRIC FLOW EQUALIZING DRIVE CONTROL WHEEL

BACKGROUND OF THE INVENTION

A typical pumping cycle of a peristaltic pump operated at a constant speed throughout an entire cycle delivers fluid at different rates throughout the cycle. Particularly, linear peristaltic pumps act upon with a plurality of sequentially actuated pumping members to move a column of fluid through the tubing. The sequentially actuated pumping members progressively close the tubing from an inlet end toward a delivery end over a short length of the tubing. After one of the pumping members squeeze the fluid downstream toward the delivery end, the last pumping member in the sequence retracts from the tubing as the first upstream pumping element closes the tubing. The cycle is repeated with each sequential pumping element closing the tubing. The cycle is repeated toward the delivery end, thereby moving another column of fluid through the tubing for delivery. When the last pumping element in the sequence begins to lift off of the tubing at the delivery end, the tubing expands and the flow of fluid temporarily diminishes while the pumping column refills. This period of slowed or stopped delivery of fluid is sometimes referred to as a "dead band."

Also to a lesser degree, during other portions of the cycle, particularly immediately before and immediately after the dead band, the amount of fluid delivered is not precisely constant throughout the entire cycle. It is desirable to avoid the slow period of the dead band particularly when the volumetric flow is low.

Various control devices have been devised for controlling the drive motors at different speeds during the different portions of the cycle. Most such control devices require complex electronic controls or relatively expensive stepper motors with controls for varying the stepper speed.

In one such mechanism, a stepper motor having a first stepping speed outside of the dead band and having a second, faster stepping speed during the dead band, was provided by dividing one complete 360° cyclic revolution of peristaltic pumping mechanism into the number of steps proportional to the angular duration of the dead band. For example, where the dead band exists during approximately 150° of rotation and the stepper motor has approximately 200 motor steps for each full 360° revolution of peristaltic drive shaft, the dead band corresponds to approximately 83 of the 200 steps of the stepper motor. A timing wheel is used comprising a transparent arc portion covering angular rotation of the wheel during which the stepper motor is to be operated at one speed and a second opaque arc portion corresponding to the angular rotation of the wheel during which the stepper motor is to be rotated at the second faster speed. Thus, a stepper motor is provided with two speeds of stepping. The transition from opaque to transparent is detected with a light sensor causing the stepping speed of the motor to transition from a first speed to a second speed. When the transition from the transparent arc to the opaque arc of the wheel is detected, the motor switched back to the first speed. This device also provided for the second sensor and a series of alternating opaque and transparent area throughout the slow pumping speed portion of the cycle for the purpose of checking for proper rotation direction. Such a device not only required a stepper motor having a variable stepping speed adjustable to correspond to the desired delivery rate and a maximum stepper speed that is activated each time the timing wheel indicates that the cycle of the pump is in the dead band. Moreover, this mechanism did not fully compensate for the variations of pumping rate during the period before and after the dead band. An attempt to compensate for these volumetric pumping rate variations was made by addressing a 150° dead band with 138° of the faster stepper speed, thus only approximating the actual variations of the rate of pumping.

SUMMARY OF THE INVENTION

The present invention overcomes many of the drawbacks of prior devices by providing a variable speed motor having a constant rotational speed at a selected fixed voltage input. A stepper motor DC is not required. A control switch circuit is connected between the motor and the fixed voltage input power, the control switch circuit is activatable in response to first electrical signals to switch the motor "on" and in response to second electrical signals to switch the motor "off." A selectable frequency, regular interval, electrical signal device is connected to the control switch circuit to provide the first electrical signals to actuate the control switch circuit to turn the motor "on." encoder wheel is coupled to the motor for rotation of the encoder wheel at the constant motor speed or at a speed proportional to the constant rotational speed of the device. The encoder wheel has a plurality of detectable areas spaced there around. In one inventive embodiment, where the rotation device is a peristaltic pump, one complete rotation of the encoder wheel advantageously constitutes one complete peristaltic pumping cycle. The detectable areas are spaced at different rotational distances apart corresponding to different amounts of the peristaltic pump rotation required for a constant flow volume during a pumping cycle. A sensor is provided to detect the detectable areas.

Advantageously, for purposes of ease of construction, the detectable areas are defined by alternately opaque and transparent portions of the wheel and the sensor is a light source and photoelectric cell operatively positioned straddling the encoder wheel and connected to the control switch circuit to provide an electrical signal to turn the motor "off" each time one of the light shines through the encoder wheel. For example, an opaque wheel may have spaced apart openings or slits there around. The motor is activated to an "on" condition at the next regular interval signal and the motor rotates the pump and the encoder wheel at a constant speed of the motor until the next detectable area of the encoder wheel is sensed. The physical spacing between each detectable area indicates the desired amount of rotation that is accomplished before the motor is turned "off" again. The motor turns "on" again only at the next regular interval and again turns "off" when the next detectable area is sensed. Thus, by spacing the detectable areas around the encoder wheel to provide the same volume of flow for each regularly timed interval, the motor moves the linear peristaltic pump mechanism an amount required to have equal volumetric flow during each regular timed interval. By spacing the detectable areas apart a greater distance during the period during the dead band, the motor will be turned "on" by the regular interval electrical signal, it will rotate the pump at the constant rotational speed of the motor until the next spaced apart detectable portion is detected and the motor is turned "off" and then the motor is turned "on" again when next regular interval electrical signal is provided. Thus, although the motor operates at a constant speed, it operates for longer or shorter periods during the rotational cycle, depending upon the space between the detectable areas on the encoder wheel to compensate for different volumetric pumping rates during the pumping cycle. The complexities and additional expense of a stepper motor is avoided.

The frequency of the regular interval is adjustable to obtain a desired total volumetric flow rate within a low range of flow rates at which the dead band might be significant. A sufficiently high constant motor speed is selected to insure that the maximum spacing (corresponding to the dead band) can be traversed during the shortest regular interval. Above the low range of flow rates controlled by the regular interval, the rotation of the variable speed DC motor is continuous throughout the pumping cycle and the speed of the variable speed DC motor and therefore the total volumetric flow rate is controlled by increasing or decreasing an uninterrupted voltage continuously supplied to the motor. Again, the complexities of having a stepper motor that operates at high rates is avoided.

The fixed constant motor speed of said low range of flow rates is achieved by selecting a nominal value for the fixed voltage input power, which in turn may be adjusted to accommodate the characteristics of a given instrument, as a means of preventing rotational overshoot due to angular momentum. This nominal fixed voltage input will be increased if the time taken to reach a given "off" position is longer than expected. The expected time is determined by the average rotational rate of the mechanism and the spacing of the given detectable area of the timing wheel. The nominal voltage can also be adjusted to eliminate excessive power consumption during the "on" condition.

BRIEF DESCRIPTION OF THE DRAWINGS

The foregoing objects, advantages, and features, as well as other objects and advantages, will become more apparent with reference to the description and drawings below, in which like numerals represent like elements and in which:

FIG. 3 is a schematic representation of the cam mechanism of the peristaltic pump, and depicting camshaft and a plurality of offset cams positioned there along in a fixed relationship with a volumetric flow equalization drive control wheel encoder according to the present invention;

FIG. 4 is a schematic representation of the comprehensive action of pumping elements of a peristaltic pump at a beginning portion of the stroke and which the volume of flow per degree of rotation is schematically depicted by the representative length of a flow arrow;

FIG. 5 is a schematic depiction of the compressive action of pumping elements of a peristaltic pump at a pumping stroke position advanced from the position depicted in FIG. 4;

FIG. 6 is a schematic depiction of a further advanced portion of the cyclic pumping stroke of a linear peristaltic pump;

FIG. 7 is a schematic depiction of a further advanced pumping stroke at which the last downstream pumping element is in a closed position simultaneously with the first upstream pumping element also in a closed position, this position corresponding to the dead zone in which the volume of flow is stopped or at least greatly diminished;

FIG. 8 is another schematic depiction of the cyclic pumping stroke at which the desired volumetric rate of flow per degree of pump rotation is again substantially reestablished;

DETAILED DESCRIPTION OF THE PREFERRED EMBODIMENTS

Figure 1:
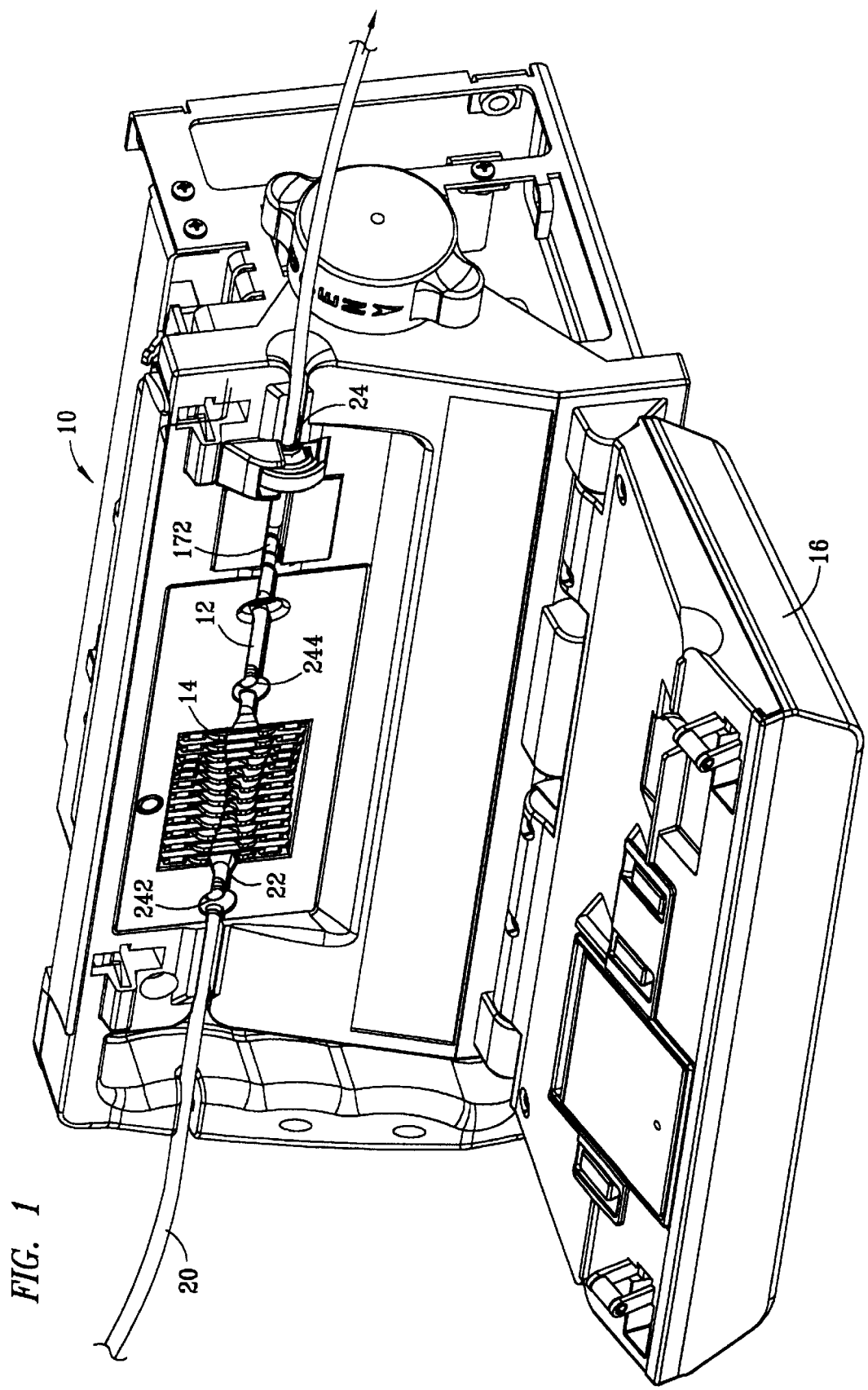
FIG. 1 is a perspective view of a linear peristaltic pump having a plurality of pumping elements for engagement along a flexible medical infusion tubing to pump a volume of fluid there along.

FIG. 1 depicts a schematic perspective view of a medical infusion pump 10 having a channel 12 formed into a face 18, along which channel is insertable so that a pump engagement portion 22 of the tubing set 20 is engaged in a linear peristaltic pumping apparatus of the pump 10. The tubing set 20 further comprises an inlet end 22 and an outlet end 24. Linear peristaltic pumping apparatus 14 acts to squeeze the tubing 20 against the door 16 when door 16 is closed against face 18 of the pump. The peristaltic pumping action is accomplished with a plurality of pumping plates, each sequentially squeezing the tubing so that a column of fluid is moved to the inside of the tubing, continuously squished from one pumping plate to the next and through the outlet 24 to the patient.

Figure 2:
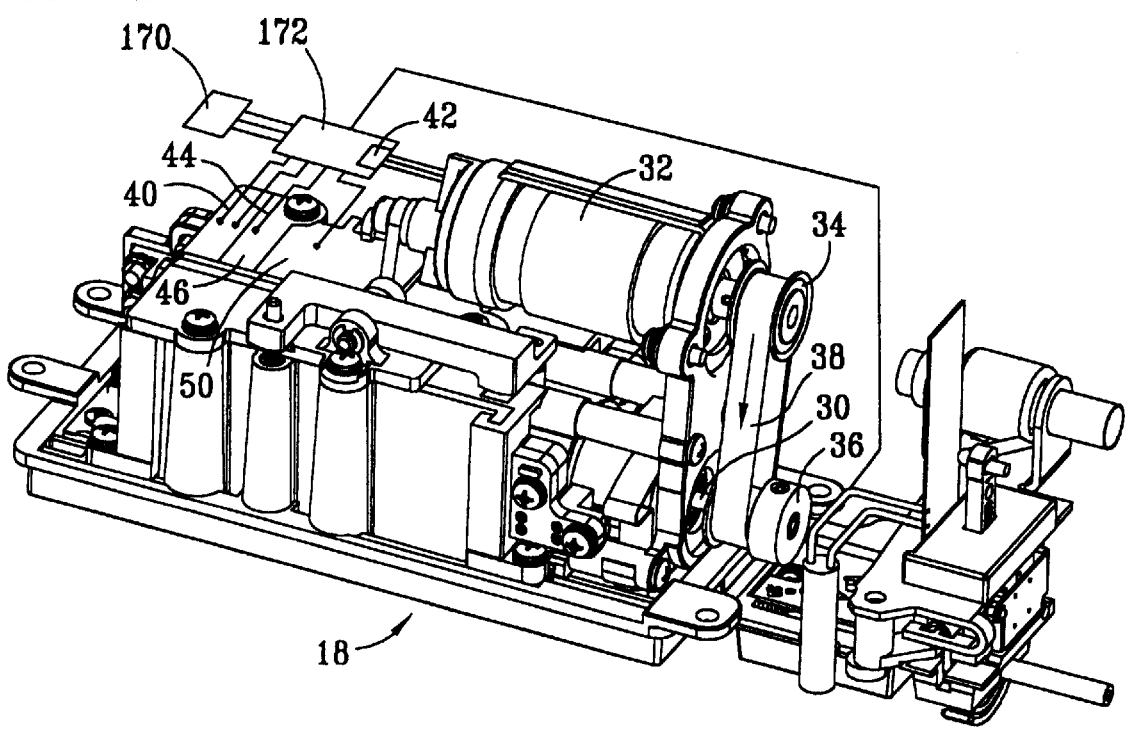
FIG. 2 is a schematic perspective view of a subassembly of the pump of FIG. 1 in which the pump is face down and further including a motor operatively engaged with camshaft of the linear peristaltic pump through a belt-and-pulley drive arrangement.

With a reference to FIG. 2, which is a perspective view of the interior of pump 10, it will be understood that the pumping plates are driven in reciprocation with cam mechanism 30 which is driven by a motor 32 variable speed DC through pulleys 34 and 36 with a continuous drive belt 38 engaged there around. Motor 32 is connected to a power supply 40 schematically represented in FIG. 2 through a "switch" circuit 42. Switch circuit 42 may be in the form of a gate array and microprocessor, and is responsive to a first electrical signal schematically represented as 44 from a constant interval frequency device 46 to turn the motor "on." Switch circuit 42 is responsive to a second electrical signal 48 from a photoelectric sensor 50 to turn the motor 32 "off." An index signal 45 is also provided from sensor 55 detecting area 82 on the encoder wheel 74.

FIG. 3 schematically depicts a perspective view of camshaft 30 cam mechanism driven by drive belt 38 and connected end pulley 36 from motor pulley 34 attached to the rotational shaft of motor 32. In the camshaft 30, it is supported with a plurality of spaced apart bearings 56 and 58 and carries a plurality of offset rotational cams 60 rigidly secured to shaft 30 rotation therewith. In the embodiment depicted, the plurality of offset cams 60 comprises twelve offset cams 61, 62, 63, 64, 65, 66, 67, 68, 69, 70, 71 and 72. Camshaft 30 also has a flow equalization encoder wheel 74 attached in a fixed angular relation to the plurality of cams 60 for rotation with camshaft 30. The encoder wheel 74 comprises a plurality of detectable areas 76 defined around the perimeter of the wheel by alternating opaque portions 78 and transparent portions 80. The opaque portion is conveniently formed by constructing the timing wheel of an opaque material, such as a metallic material, and the transparent areas are conveniently formed by cutting appropriately sized and spaced slots 80 around the periphery of the encoder wheel 74. Additionally, for purposes that will be discussed more fully below, a synchronizing area 82 may be advantageously formed in encoder wheel 74 to be detected with additional sensor 51 comprising a light source 53 and a photocell 55. As depicted in FIG. 3 an initialization wheel 84 or synchronization is connected to the camshaft 30 through a clutch mechanism 86. The synchronization wheel 84 has a position locating notch 88 that is appropriately detected with a sensor.

The plurality of rotary cams 60 engaged plurality of pumping members 90 and rotation of camshaft 30 causes the pumping members to sequentially act against the tubing 20 to provide a peristaltic pumping action.

FIG. 4 schematically depicts a portion of a peristaltic pumping cycle at which the upstream pumping members 92 and 93 have closed tubing 20 and the further downstream pumping finger 94, 95, 96, 97, 98, 100, 101 and 102 are raised a sufficient amount to allow the column of fluid 104 to be moved downstream. With reference to FIG. 4 and flow arrow 106 is schematically depicted with a link indicating the quantity of fluid flow caused by rotating camshaft 30 through a fixed amount of angular rotation.

FIG. 5 depicts pumping action against tube 20 after cam 30 has been rotated an additional amount. Middle pumping members 96 and 97 have compressed the tubing 20 closed and column of fluid 108 is being squeezed downstream. Again, the volumetric flow for a predetermined angular rotation theta ($\theta$) of camshaft 30 as depicted by flow arrow 110. It is noted that the volume of flow 106 and 110 are substantially equivalent when the pumping action is in the middle range, as depicted in FIGS. 4 and 5.

FIG. 6 depicts an advanced portion of the pumping cycle in which pumping fingers 100 and 101 have compressed tubing 20 to close position and the column of fluid 112 remains to be moved by further compression by pumping element 101 and 102 is diminished slightly so that the volumetric flow per angular rotation depicted with arrow 114 is slightly diminished from that as depicted with arrows 110 and 106.

FIG. 7 depicts the end and also the beginning of a pumping cycle in which the first upstream pumping element 91 and the last downstream pumping element 102 have the tubing 20 compressed to a closed condition. At this position, there is no additional column of fluid 116 to be advanced by further rotation of the camshaft. The flow is substantially diminished or reduced, as indicated by flow arrow 118. Referring again to FIG. 8, pumping element 102 begins to lift and pumping elements 92 and 93 begin to compress the fluid again so that volumetric flow begins to increase in the column 120 of fluid is moved downstream at flow rate for a given angular rotation theta, ($\theta$) as depicted by arrow 122, thus, immediately ahead and behind the portion of the pumping cycle indicated by FIG. 7, i.e., the dead band, the amount of flow per angular rotation theta ($\theta$) of camshaft 30 is slightly diminished from the midrange pumping flow as depicted in FIGS. 4 and 5.

Figure 9:
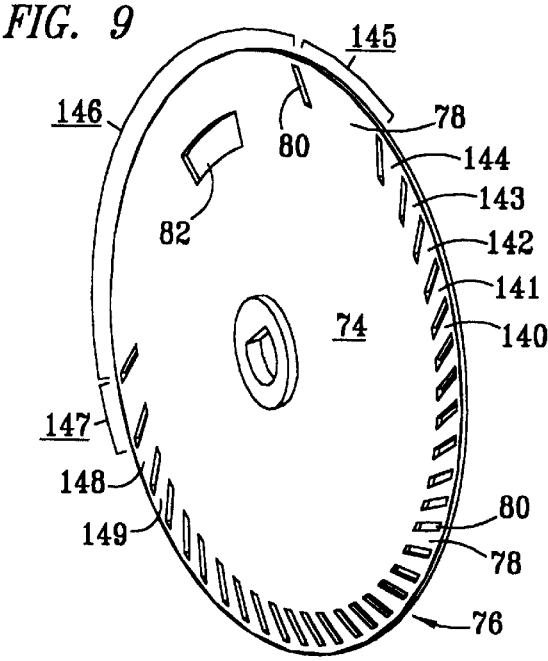
FIG. 9 is an enlarged schematic depiction of the timing wheel of FIG. 3 with a plurality of detectable open areas spaced around the circumference and depicting the different spacing between the detectable areas around the circumference of the encoder wheel according to the present invention.

To compensate for this dead band, the timing wheel 74 is advantageously constructed as depicted in FIG. 9, which is an end view of camshaft 30 with the timing wheel 74 attached thereto. In the embodiment depicted in FIG. 9, the pumping cycle has been divided into thirty-two increments. Each increment to be provided with the same volume of flow when the pump is operating in a low range between about 0.1 ml./hour and up to between about 80 and 160 ml./hour. Thus, for example, in a linear peristaltic pump adapted for a particular size of tubing in which each complete pumping cycle, i.e., one rotation of the camshaft provide 0.144 ml./cycle then each ¹⁄₃₂ of the cycle would be required to produce 0.0045 ml. It will require substantially greater angular movement in the dead zone to produce the 0.0045 ml. than it will in the middle pumping range as described above with respect to FIGS. 4–8. Similarly, immediately ahead and immediately following the dead band, the rate of pumping per angle of rotation is slightly diminished so that an additional spacing distance is provided on encoder wheel 74 corresponding to those areas. The precise spacing for obtaining each desired amount of pumping fluid can be empirically obtained in the aforegiven pump design and the slots can be appropriately cut into the encoder wheel so that constant volumetric flow rate is obtained in the desired low volume pumping range.

Figure 10:
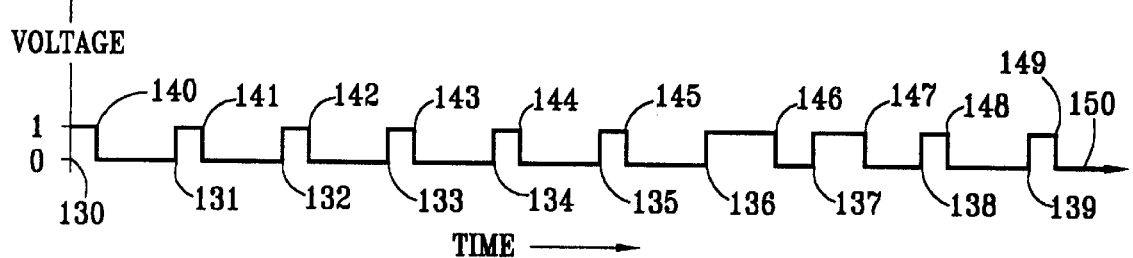
FIG. 10 is a graphical representation of the "on" and "off" signals received by the pump operating at a fixed voltage producing a constant motor variable speed DC speed when the motor is "on" and turning the motor "off" when the next detectable area is sensed so that a constant volumetric flow rate is produced.

Referring to FIG. 10, the operation of the pump with encoder wheel is schematically represented in which the initiation of time intervals are indicated by lines 130–139 along a time axis 150 and the motor speed is represented by the voltage depicted here as one unit and the duration of the pumping to obtain the desired volumetric flow is indicated by the duration of the "on" time 140–149 before the motor is turned "off" by the sensor 50 detecting the next dectable area or slot.

Figure 11:
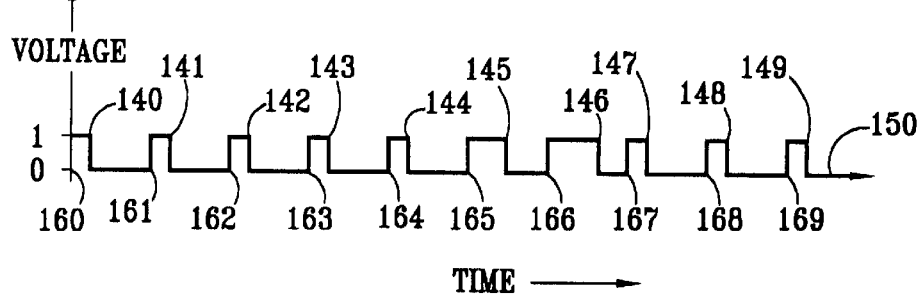
FIG. 11 is a schematic representation of the "on" and "off" signals received by the pump motor for producing a desired constant flow rate greater than the volumetric flow rate depicted in FIG. 10.

FIG. 11 depicts an increased volumetric flow rate in which the volume or flow rate is increased by increasing the frequency of equal time intervals 160–169. The "on" time 140–149 continues to be sufficiently long to provide equivalent 0.0045 ml. per the amount or rotation of the pump as determined by the space between the timing slots. Because the 0.0045 ml. is achieved during each equivalent time interval, the flow to the patient is substantially continuous and at a constant volumetric flow rate throughout the entire pumping cycle.

Figure 12:
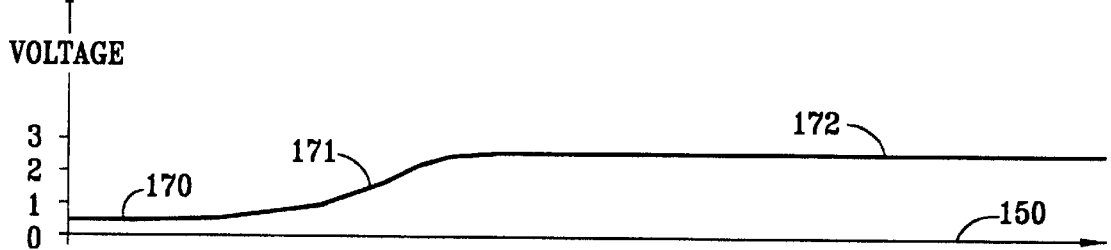
FIG. 12 is a schematic representation of a variable voltage power signal received by the motor when the total volumetric flow rate is greater than a predetermined rate at which the effect of any dead band in the pumping cycle is deemed to be insignificant.

FIG. 12 depicts a control voltage varied from 170 to 171 to 172 for the pumping motor when the total desired volumetric flow rate exceeds the low range in which the dead zone is deemed to be significant. It has been found that the dead zone is not significant above about 80–160 ml./hour for a pump constructed according to the example set forth above because each pump cycle is very short. For example, at 160 ml./hour the pump will rotate more than 1100 times every hour or about 18 times per minute so that each cycle takes about three and one-half seconds so that the dead zone is not longer than one second. At higher rates, the dead zone is even shorter.

Figure 13:
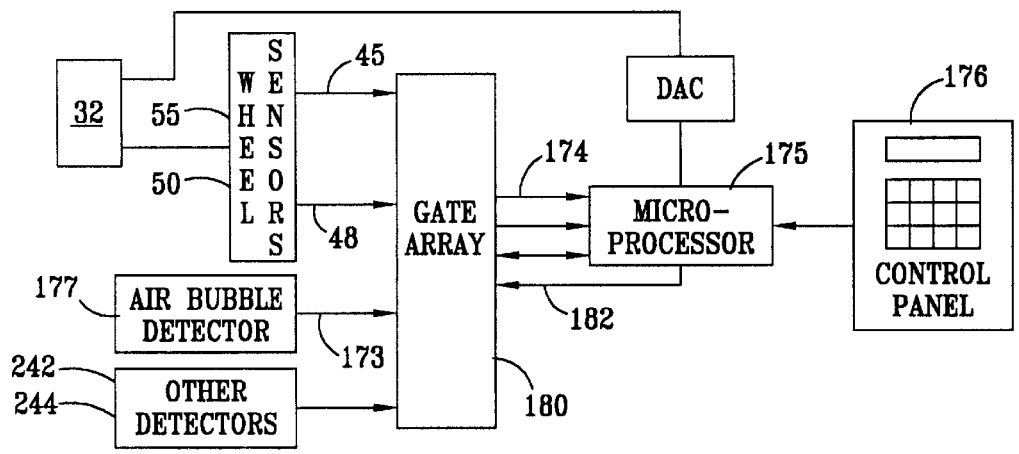
FIG. 13 is a schematic block diagram of certain aspects of control circuitry for a linear peristaltic pump.

With reference to FIG. 13 it will be further understood that the encoder wheel has other functions besides controlling fluid flow. It is also used to synchronize certain monitor tasks in a microprocessor 175, such as measuring air bubbles with an air bubble detector 177 that is positioned along channel 12, and other detection functions 174, as for example monitoring and/or calculating fluid pressure from measurements at sensor 242 and 244, and etc. These microprocessor tasks are initiated by interrupts 174 which are generated from the encoder wheel slot sensor 50. Since the detectable areas of the flow control encoder wheel are spaced so as to represent areas of equal volume, this allows the accurate detection of air bubbles of a certain volume, by checking the air detector 177 at each encoder slot.

A control panel 176 is provided by which an operator can input a desired volumetric flow to microprocessor 175. At high delivery rates, the microprocessor 175 may not have time to perform all of the above-mentioned tasks for every encoder slot signal 48. The rate of data can overload the microprocessor with too much data. Also, at high flow rates, there is a lesser need for as many slots in the timing wheel for the purpose of flow control. Therefore, an intermediate device, preferably a gate array 180 is used to select which of the thirty-two encoder slot signals will actually result in a microprocessor interrupt. This microprocessor can command the gate array with a signal known as a command byte 182 to generate an interrupt for every encoder slot signal, every second encoder slot signal or every fourth encoder slot signal, depending on the selected delivery rate. Other divisors could also have been implemented. This saves CPU processing time so that a slower CPU speed can be used.

When the gate array has been commanded to only generate interrupts for every other encoder slot signal or every fourth encoder slot signal, the resolution of certain measurement tasks performed by the microprocessor may be compromised, e.g., measurement of air bubbles in the line. Therefore tasks that require high resolution measurements may be performed within the gate array 180, still synchronized by the encoder slot signals. For example, tasks performed within the gate array could be performed at every encoder slot signal while microprocessor interrupts are only generated for every second encoder slot signal or every fourth encoder slot signal. This would provide the pump with the same benefits that would be derived from multiple encoder wheels with only one encoder wheel such as the single flow control encoder wheel.

FIG. 13 is a schematic block diagram of certain aspects of control circuitry for a linear peristaltic pump.

Figure 14:
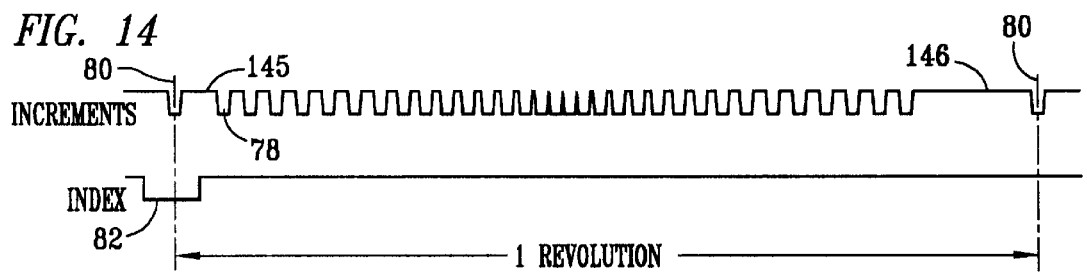
FIG. 14 is a graphical representation of the controlled movement of a linear peristaltic pump in response to input from a volumetric flow equalizing drive control wheel encoder as synchronized with the index indicator on the encoder wheel for one complete revolution or one pumping cycle.

FIG. 14 is a graphical representation of the controlled movement of a linear peristaltic pump in response to input from a volumetric flow equalizing drive control encoder wheel as synchronized with the index indicator on the control encoder wheel for one complete revolution or one pumping cycle.

Figure 15:
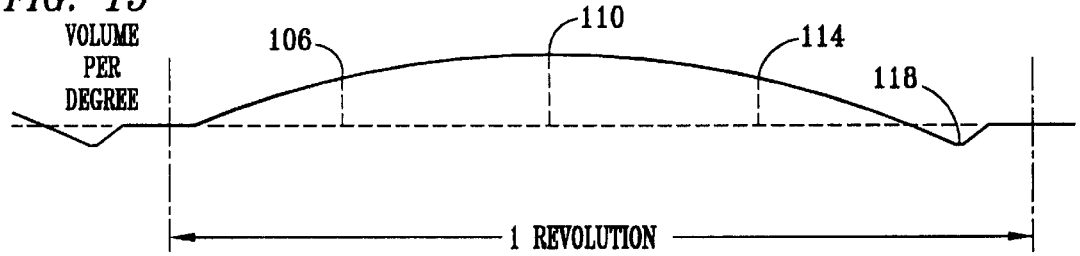
FIG. 15 is a schematic representation of the volume of flow per degree of revolution through an entire cycle of the linear peristaltic pump.

FIG. 15 is a schematic representation of the volume of flow per degree of revolution through an entire cycle of the linear peristaltic pump.

Figure 16:
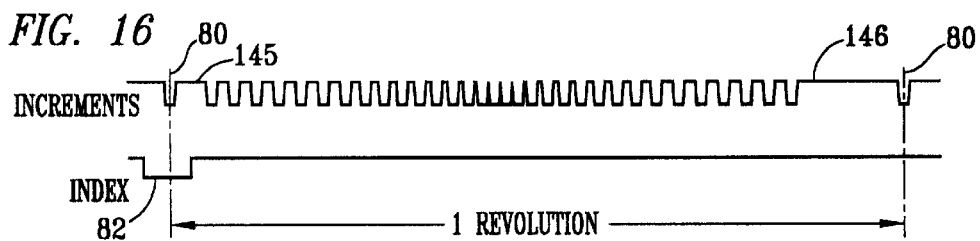
FIG. 16 is a graphical representation of the movements of a linear peristaltic pump controlled by the encoder wheel or the volumetric flow equalizing drive control encoder wheel in which the rate of pumping is increased as indicated by the shortened time duration for one complete revolution.

FIG. 16 is a graphical representation of the movements of a linear peristaltic pump controlled by the encoder wheel or the volumetric flow equalizing drive control wheel in which the rate of pumping is increased as indicated by the shortened time duration for one complete revolution.

Figure 17:
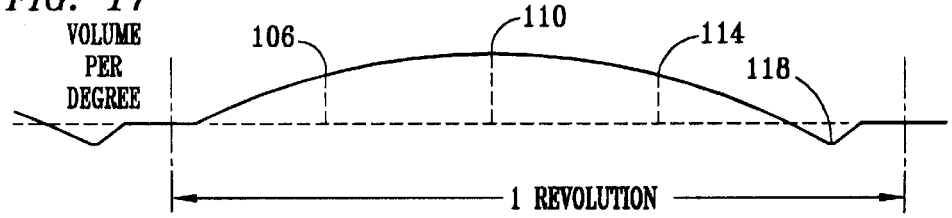
FIG. 17 is the volume per degree of pump rotation for an entire revolution of the pump corresponding to a revolution completed in the same shortened time as in FIG. 16.

FIG. 17 is the volume per degree of pump rotation for an entire revolution of the pump corresponding to a revolution completed in the same shortened time as in FIG. 16.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A rotation control for a device to be rotated comprising:
 a. a variable speed DC motor having a constant rotational speed upon receiving a selected fixed voltage electrical input power;
 b. an adjustable electrical input power supply connected to said motor for supplying selectably said selected fixed voltage;
 c. a switch circuit connected between said motor and said power supply activatable in response to a first electrical signal to turn said motor "on" and activatable in response to a second electrical signal to turn said motor "off";
 d. a selectable frequency, regular interval electrical signal device connected to said switch circuit to provide a series of said first electrical signals at regular timed intervals to activate said switch circuit to turn said motor "on";
 e. an encoder wheel coupled to said device to be rotated and to said motor for rotation of said encoder wheel at a speed proportional to said constant rotational speed of said motor, said encoder wheel having a plurality of openings around said encoder wheel with predetermined varied spacing there between, said spacing corresponding to a desired amount of device rotation during that part of the rotation of said encoder wheel; and
 f. a light sensor operatively positioned adjacent said encoder wheel for detecting said spaced openings and connected to said switch circuit to provide second electrical signals to turn said motor off when a subsequent one of said openings is detected by said sensor thereby allowing said device to traverse said desired amount of device rotation between said spaced-apart opening during said regular timed intervals.

2. A rotation control for a device to be rotated as in claim 1 further comprising:
 a) an indexing opening at one position on said encoder wheel;
 b) another light sensor operatively positioned adjacent to said encoder wheel for detecting said index opening and to provide a signal to said device for repeatedly synchronizing control of said motor with said encoder wheel.

3. A rotation control for a device to be rotated as in claim 1 wherein said switch circuit comprises a gate array coupled between said electrical signals to turn said motor on and off and a microprocessor.

4. A rotation control for a device to be rotated as in claim 3 wherein said gate array is responsive to a command signal from said microprocessor to interrupt said motor control only after skipping a predetermined number of sensory signals from said detection of said openings around said encoder wheel.

5. A rotation control for a device to be rotated as in claim 1 further comprising
 a) a control panel by which an operator can input a desired volumetric flow rate; and b) a microprocessor responsive to said signals from said regular intervals, to said signals from said light sensor and to said input desired volumetric flow rate from a control panel to operate said device to be rotated according to said encoder wheel electrical signals below a predetermined desired input flow rate and for controlling said motor speed with a continuous voltage power above said predetermined desired input flow rate.

6. A rotation control for a device to be rotated as in claim 5 wherein said predetermined desired input flow rate is in the range of about 80 ml./hour to about 160 ml./hour.

7. A linear peristaltic pump having rotation control comprising;

a) a rotary cam mechanism operably connected to pumping fingers for successfully acting against a flexible tubing to pump fluid therethrough;

b) a variable speed DC motor connected for rotating said rotary cam mechanism, said DC motor having a constant rotational speed upon receiving a selected fixed voltage electrical input power;

c) an adjustable voltage electrical input power supply for adjustably supplying a fixed voltage connected to said variable speed DC motor for supplying selectably said selected fixed voltage to said variable speed DC motor;

d) a switch circuit connected between said variable speed DC motor and said power supply activatable in response to a first electrical signal to turn said variable speed DC motor "on" and activatable in response to a second electrical signal to turn said variable speed DC motor "off";

e) a selectable frequency, regular interval electrical signal device connected to said switch circuit to provide a series of said first electrical signals at regular timed intervals to activate said switch circuit to turn said variable speed DC motor "on";

f) encoded wheel coupled to said linear peristaltic pump and to said variable speed DC motor for rotation of said encoder wheel at a speed proportional to said constant rotational speed of said variable speed DC motor, said encoder wheel having a plurality of openings around said encoder wheel with predetermined, differing spacing there between, said spacing corresponding to a desired amount of device rotation, wherein said predetermined differing spacing provides approximately equal delivery volume increments of fluid pumped through said flexible tubing; and g) a light sensor operatively positioned adjacent said timing wheel for detecting said spaced openings and connected to said switch circuit to provide a second electrical signal to turn said variable speed DC motor off when a subsequent one of said openings is detected by said sensor thereby allowing said pump to traverse said desired amount of rotation of said pumping cam to provide said approximately equal delivery volume increments of pumped fluid during said regular timed intervals.

8. A linear peristaltic pump as in claim 7 further comprising:

a) an indexing opening at one position on said encoder wheel;

b) another light sensor operatively positioned adjacent to said encoder wheel for detecting said index opening and to provide a signal to said pump for repeatedly synchronizing control of said motor with said encoder wheel.

9. A a linear peristaltic pump as in claim 7 wherein said switch circuit comprises a gate array coupled between said electrical signals to turn said motor on and off and a microprocessor.

10. A linear peristaltic pump as in claim 9 wherein said gate array is responsive to a command signal from said microprocessor to interrupt said motor control only after skipping a predetermined number of sensory signals from said detection of said openings around said encoder wheel.

11. A rotation control for a linear peristaltic pump as in claim 1 further comprising a) a control panel by which an operator can input a desired volumetric flow rate; and b) a microprocessor responsive to said first electrical signals from said regular intervals, to said second electrical signals from said light sensor and to said input desired volumetric flow rate from said control panel to operate said device to be rotated according to said first and second electrical signals below a predetermined desired input flow rate and for controlling the speed of said variable speed DC motor with a continuous voltage power above said predetermined desired input flow rate.

12. A rotation control for a linear peristaltic pump as in claim 11 wherein said predetermined desired input flow rate is in the range of about 80 ml./hour to about 160 ml./hour.

* * * * *

UNITED STATES PATENT AND TRADEMARK OFFICE
CERTIFICATE OF CORRECTION

PATENT NO. : 6,064,797
DATED : May 16, 2000
INVENTOR(S) : Joe C. Crittendon; Harry C. Copp; Roberta Stavely; David L. Harrison It is certified that error appears in the above-identified patent and that said Letters Patent is hereby corrected as shown below:

ABSTRACT
Line 14, replace "timing disk" with -- encoder wheel --.
Line 16, replace "timing disk" with -- encoder wheel --.
Line 17, replace "disk" with -- wheel --.

DRAWINGS
Figure 1, the reference numeral "172" should read -- 177 --.
Figure 2, the reference numeral "170" should read -- 175 -- and the reference numeral "172" should read -- 180 --.

SPECIFICATION
Column 2,
Line 20, insert -- An -- immediately before "encoder wheel".

Column 4,
Line 1, replace "timing" with -- encoder --.
Lines 27-28, replace "wheel encoder" with -- encoder wheel --.

Column 5,
Line 8, the phrase "camshaft 30 cam mechanism" should read -- cam mechanism camshaft 30 --.
Line 31, replace "initialization" with -- synchronization --.
Line 32, delete "or synchronization".

UNITED STATES PATENT AND TRADEMARK OFFICE
CERTIFICATE OF CORRECTION

PATENT NO.  : 6,064,797
DATED       : May 16, 2000
INVENTOR(S) : Joe C. Crittendon; Harry C. Copp; Roberta Stavely; David L. Harrison It is certified that error appears in the above-identified patent and that said Letters Patent is hereby corrected as shown below:

Column 6,
Line 48, replace "dectable" with -- detectable --.

CLAIMS

Column 9,
Line 37, replace "encoded" with -- an encoder --.

Signed and Sealed this

Seventh Day of August, 2001

*Attest:*

*Attesting Officer*

NICHOLAS P. GODICI
*Acting Director of the United States Patent and Trademark Office*